(12) United States Patent
Beckmann et al.

(10) Patent No.: US 7,128,814 B2
(45) Date of Patent: *Oct. 31, 2006

(54) PROCESS FOR SEPARATING 2-BUTANOL FROM TERT-BUTANOL/WATER MIXTURES

(75) Inventors: Andreas Beckmann, Recklinghausen (DE); Dieter Reusch, Marl (DE)

(73) Assignee: OXENO Olefinchemie GmbH, Marl (DE)

( * ) Notice: Subject to any disclaimer, the term of this patent is extended or adjusted under 35 U.S.C. 154(b) by 182 days.

This patent is subject to a terminal disclaimer.

(21) Appl. No.: 10/790,707

(22) Filed: Mar. 3, 2004

(65) Prior Publication Data

US 2004/0200716 A1 Oct. 14, 2004

(30) Foreign Application Priority Data

Mar. 22, 2003 (DE) ................. 103 12 918

(51) Int. Cl.
*B01D 3/42* (2006.01)
*C07C 29/82* (2006.01)

(52) U.S. Cl. .................. 203/2; 203/3; 203/18; 203/77; 203/80; 203/DIG. 9

(58) Field of Classification Search .............. 203/2, 203/3, 18, 74, 77, 80, 99, DIG. 19, DIG. 9; 568/913

See application file for complete search history.

(56) References Cited

U.S. PATENT DOCUMENTS

| | | | | |
|---|---|---|---|---|
| 4,371,427 A | * | 2/1983 | Holler et al. ................. | 203/3 |
| 4,902,385 A | * | 2/1990 | Osterburg ................... | 203/96 |
| 5,332,478 A | * | 7/1994 | Berg ........................... | 203/58 |
| 5,368,699 A | * | 11/1994 | Rhiel et al. .................. | 203/2 |
| 5,658,435 A | * | 8/1997 | Berg ........................... | 203/57 |
| 5,759,359 A | * | 6/1998 | Berg ........................... | 203/57 |
| 5,985,100 A | * | 11/1999 | Aron et al. .................. | 203/74 |
| 6,413,378 B1 | * | 7/2002 | Kanauchi et al. ............ | 203/1 |

OTHER PUBLICATIONS

Office Action as received in corresponding Chinese Application No. 200310120350.3 dated Apr. 7, 2006 w/English Translation.
Li Fengyun, Journal of Fushun Petroleum College, 18(4): 28-30 w/English Abstract.
Guo Yufeng et al, Petrochemical Technology and Application, 17(2):114-117 w/English Abstract.
Database Chemabs 'Online! Chemical Abstracts Service, Columbus, Ohio, US; Inashima, Makoto et al: "Purification of a crude tert-butyl alcohol" XP002279771 gefunden im STN—Database accession No. 1975:605762 "Zusammenfassung" & JP 500 163 39B B4 (Maruzen Oil Company, Ltd., Japan) Jun. 1975 (Jun. 12, 1975).

\* cited by examiner

*Primary Examiner*—Virginia Manoharan
(74) *Attorney, Agent, or Firm*—Oblon, Spivak, McClelland, Maier & Neustadt, P.C.

(57) ABSTRACT

The present invention relates to a process for separating 2-butanol from tert-butanol/water by adding of tert-butanol such that the water concentration lowers to less than the limit concentration of the distillation boundary line connecting the two azeotropes TBA/water and SBA/water and is subsequently worked up by distillation.

16 Claims, 2 Drawing Sheets

PROCESS FOR SEPARATING 2-BUTANOL FROM TERT-BUTANOL/WATER MIXTURES

BACKGROUND OF THE INVENTION

1. Field of the Invention

The present invention relates to a process for separating 2-butanol (also referred to below as secondary butanol or SBA) from tert-butanol/water mixtures which are obtained in the dissociation of tert-butanol (TBA), in particular tert-butanol prepared from industrial C4-hydrocarbon mixtures, into isobutene and water.

2. Discussion of the Background

Isobutene is a starting material for the production of butyl rubber, polyisobutylene, isobutene oligomers, branched C5-aldehydes and C5-carboxylic acids. It is also used as an alkylating agent and as intermediate for the preparation of peroxides.

In industrial streams, isobutene is present together with saturated and unsaturated C4-hydrocarbons. Isobutene cannot be separated economically from these mixtures by distillation because of the small boiling point difference or the very low separation factor between isobutene and 1-butene. Isobutene is therefore isolated from industrial hydrocarbon mixtures by converting isobutene into a derivative which can easily be separated off from the remaining hydrocarbon mixture and redissociating the isolated derivative into isobutene and the derivative-forming agent.

The following procedure is usually employed to separate isobutene from C4 fractions, for example the C4 fraction from a steamcracker. After the major part of the multiply unsaturated hydrocarbons, mainly butadiene, has been removed by extraction (or extractive distillation) or selective hydrogenation to linear butenes, the remaining mixture (raffinate I or hydrogenated cracking C4) is reacted with alcohol or water. Use of methanol as alcohol gives methyl tert-butyl ether (MTBE) and use of water gives tert-butanol (TBA). After they have been separated off, both products can be dissociated to give isobutene in a reversal of their formation.

The dissociation of TBA is easier to carry out than the dissociation of MTBE and gives smaller amounts of by-products and is thus the preferred method of isolating isobutene. The dissociation of TBA is preferably carried out in the gas or liquid phase in the presence of an acid with partial conversion of TBA.

If isobutene-containing hydrocarbon streams in which linear butenes are also present are used for preparing TBA from isobutene, small amounts of 2-butanol (SBA) are also formed.

Whether this presents any further problem depends on how the resulting reaction mixture is worked up to give pure TBA or a TBA/water azeotrope. Owing to the low 2-butanol content of the reaction mixture, the maximum permissible 2-butanol concentration of, for example, 0.2% by mass in the TBA or in the TBA/water azeotrope is not exceeded.

If, however, the industrial TBA or TBA/water azeotrope is partially dissociated into isobutene and water, separating off the isobutene formed results in a TBA/water mixture enriched in 2-butanol (SBA). This mixture is unsuitable for the preparation of commercial quality TBA or TBA/water azeotrope without 2-butanol being separated off. It is likewise not practical to prepare isobutene from this mixture, because an increasing 2-butanol content also results in an increase in the concentration of linear butenes in the isobutene, so that the specification of the latter cannot be achieved. It is therefore necessary to discharge part of the 2-butanol while avoiding losses of TBA.

In a process for separating SBA from mixtures of SBA, TBA, and water without losses of TBA, however, it is difficult to separate by distillation since this three-component system displays a distillation boundary line which connects the binary water/TBA azeotrope at about 11% by mass of water (the literature reports values at atmospheric pressure of from 10 to 12.5% by mass) (point B in FIG. 1) and the binary water/SBA azeotrope at about 28% by mass of water (the literature reports values at atmospheric pressure of from 26.7 to 32% by mass) (point C in FIG. 1). This distillation boundary line separates two distillation fields. The above three-component system, shown in FIG. 1, thus displays two distillation fields: distillation field 1 in the region A-B-C-A and distillation field 2 in the region B-E-D-C-B. In the distillation field 1, the high boiler is water, the low boiler in this region is the TBA/water azeotrope and the intermediate boiler is the SBA/water azeotrope which cannot be separated off in pure form.

To discharge SBA from an integrated TBA-isobutene plant, it is most economical to use the stream which is richest in SBA for this purpose. However, the streams obtained in the dissociation of TBA have a relatively low SBA content. They usually have compositions lying in the distillation field 1. These streams usually further comprise small amounts of additional substances whose presence need not, however, be considered in this context. If an attempt is made to work up such a mixture having a composition in the region of distillation field 1 by distillation, it is possible either to isolate pure water as high boiler and a mixture of SBA/TBA/water as top fraction or else obtain the TBA/water azeotrope as lowest-boiling mixture in the distillate from a column and obtain a higher-boiling mixture comprising SBA/TBA/water with a high water content at the bottom. Thus, for mass balance regions and owing to the unfavorable position of the distillation lines, the SBA content cannot be increased sufficiently for discharge of this stream to be economically viable. The miscibility gap in the system (cf. FIG. 1: C-F-G-C) can also not be used economically for separation of the components or increasing their concentration.

SUMMARY OF THE INVENTION

It has surprisingly been found that SBA can be separated off from a production stream which comprises water, SBA and TBA and whose composition lies in the region of distillation field 1, in particular a production stream which is enriched in SBA, virtually without losses of TBA when TBA is added to the production stream used as feed mixture in such an amount that the mixture obtained has a composition lying in the region of the distillation field 2 and the mixture can thus be separated into SBA and a TBA/water mixture by distillation.

The invention accordingly provides a process for separating SBA from an industrial mixture which comprises SBA, TBA and water and in which the proportion by mass of water is greater than the limit concentrations of the distillation boundary line connecting the two azeotropes TBA/water and SBA/water, i.e. the SBA/TBA/water composition of the mixture lies in the region of the distillation field 1, wherein the concentration of water in the mixture is reduced by addition of TBA to such an extent that the mixture obtained has, in terms of its SBA/TBA/water composition, a proportion by mass of water which is less than the limit concentration of the distillation boundary line connecting the two azeotropes TBA/water and SBA/water, i.e. in terms of its SBA/TBA/water composition lies in the region of distillation field 2, and this mixture is separated by distillation into a stream comprising SBA and a stream comprising predominantly TBA and water.

Thus, in the process of the invention, the SBA is separated off from a mixture which, in terms of the three-component system SBA/TBA/water, lies in the distillation field 1 by addition of a TBA-containing stream to this mixture, as a result of which the composition of the three-component system is shifted into the distillation field 2, and subsequent distillation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The process of the invention makes it possible to separate SBA from mixtures which comprise SBA, TBA and water and in which the proportion by mass of water is greater than the limit concentrations of the distillation boundary line connecting the two azeotropes TBA/water and SBA/water, so that they cannot be separated purely by distillation. The use of a TBA-containing stream which preferably contains less than 12% by mass of water and possibly small amounts of high boilers (e.g. $C_8$- or $C_{12}$-hydrocarbons formed by oligomerization of isobutene, $C_8$-alcohols) and/or small amounts of low boilers (e.g. isobutene or other $C_4$-hydrocarbons) for changing the concentration in the mixture enables the use of entrainers or other extraneous substances to be dispensed with, so that a costly removal of these auxiliaries can be avoided and there is no risk of contamination of the products by these auxiliaries during the work-up. This TBA stream is preferably obtained from a plant for preparing anhydrous TBA.

In the process of the invention for separating 2-butanol (SBA) from an industrial mixture which comprises 2-butanol, tert-butanol (TBA) and water and in which the proportion by mass of water in the mixture is greater than the limit concentrations of the distillation boundary line connecting the two azeotropes TBA/water and SBA/water, i.e. the SBA/TBA/water composition of the mixture lies in the region of the distillation field 1, the concentration of water in the mixture is reduced by addition of a TBA-containing stream to such an extent that the mixture obtained has, in terms of its SBA/TBA/water composition, a proportion by mass of water which is less than the limit concentration of the distillation boundary line connecting the two azeotropes TBA/water and SBA/water, i.e. in terms of its SBA/TBA/water composition lies in the region of distillation field 2, and this mixture is separated by distillation into a stream comprising SBA and a stream comprising TBA and water.

Figure 1:
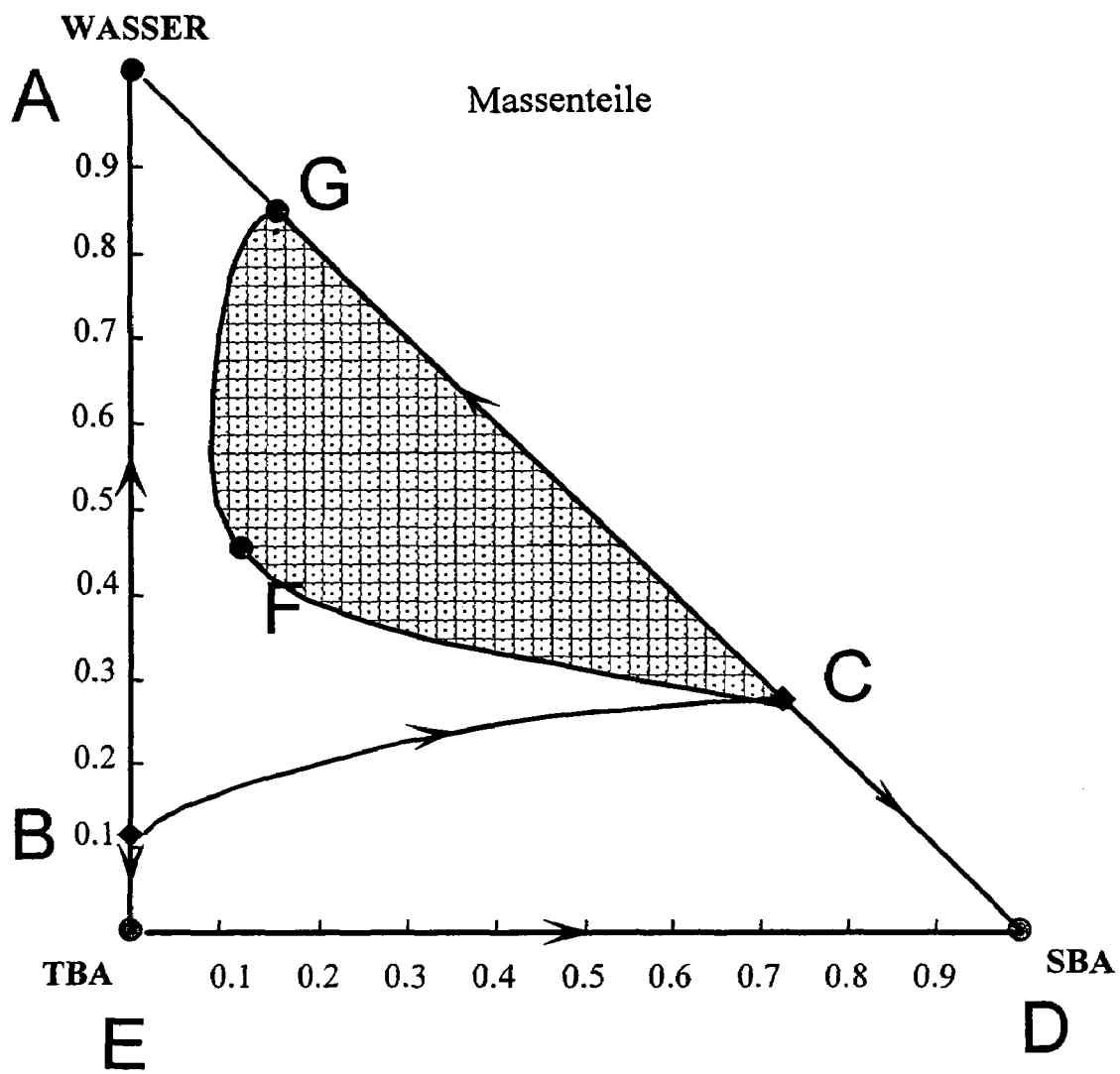
FIG. 1 depicts relative SBA, TBA, and water, in parts by mass, and the azeotropes water/TBA and water/SBA in a distillation of a mixture containing SBA, TBA, and water. Distillation boundary lines which defined distillation fields 1 and 2 are indicated.

As used herein, "distillation boundary line connecting an azeotrope of tert-butanol and water and an azeotrope of 2-butanol and water" means the line which connects the binary water/TBA azeotrope at about 11% by mass of water (the literature reports values at atmospheric pressure of from 10 to 12.5% by mass) (point B in FIG. 1) and the binary water/SBA azeotrope at about 28% by mass of water (the literature reports values at atmospheric pressure of from 26.7 to 32% by mass) (point C in FIG. 1). This distillation boundary line separates two distillation fields. The above three-component system, shown in FIG. 1, thus displays two distillation fields: distillation field 1 in the region A-B-C-A and distillation field 2 in the region B-E-D-C-B. In the distillation field 1, the high boiler is water, the low boiler in this region is the TBA/water azeotrope and the intermediate boiler is the SBA/water azeotrope which cannot be separated off in pure form.

Preference is given to adding a TBA-containing stream which has a water content of less than 12% by mass, preferably less than 10% by mass and particularly preferably less than 5% by mass. The TBA-containing stream can comprise from 90 to 99.99% of TBA. Apart from TBA and possibly water, the TBA-containing stream can possibly also contain small amounts (of from 0.0001 to 5% by mass) of high boilers (e.g. $C_8$- or $C_{12}$-hydrocarbons formed by oligomerization of isobutene, $C_8$-alcohols) and/or low boilers (e.g. isobutene or other $C_4$-hydrocarbons).

It can be advantageous for water to be removed from the industrial mixture by distillation prior to addition of the TBA-containing stream. Distillation of the industrial mixture separates it into a water-rich bottom product and a top product which has a water content which, although it is greater than the limit concentration of the distillation boundary line connecting the two azeotropes TBA/water and SBA/water, i.e. in terms of its SBA/TBA/water composition lies in the region of distillation field 1, is lower than the original concentration of water. The industrial mixture which has been pretreated in this way is then worked up according to the invention by addition of a TBA-containing stream. This procedure has the advantage that only a relatively small amount of TBA-containing stream has to be added to change the concentration of the mixture so that it lies in the region of distillation field 2.

The mixture to which a TBA-containing stream has been added and which is worked up by distillation preferably has a water content of less than 10% by mass, based on the three-component system SBA/TBA/water. However, it is important that in terms of its water content, the mixture lies in the distillation field 2, i.e. has a proportion by mass of water which is less than the water content of a mixture having a composition corresponding to the distillation boundary line B-C connecting the azeotropes SBA/water and TBA/water. The water content based on the three-component system SBA/TBA/water at SBA contents of from 0.0001 to 6% by mass is preferably less than 11% by mass, preferably less than 10% by mass and particularly preferably less than 9.5% by mass. At SBA contents of from 6.01 to 15% by mass, the water content based on the three-component system SBA/TBA/water is preferably less than 15% by mass, more preferably less than 14% by mass and particularly preferably less than 13% by mass. In addition, the mixture can further comprise up to 5% by mass, preferably up to 3% by mass, very particularly preferably from 2.5 to 0.01% by mass, of additional substances, for example $C_8$-olefins or $C_8$-alcohols.

In the process of the invention, the mixture to which a TBA-containing stream has been added is preferably fractionally distilled to give a 2-butanol-containing fraction which contains less than 1% by mass, preferably less than 0.5% by mass, of tert-butanol. The 2-butanol which is separated off in the work-up by distillation can be taken off from the vapor phase of a vaporizer of a column or in gaseous or liquid form as a side stream from the stripping section of this column.

At least part of the top product obtained as distillate in the fractional distillation of the mixture to which a TBA-containing stream has been added can be mixed into the industrial mixture to which a TBA-containing stream is added. Depending on the initial concentration of the industrial mixture and any removal of water by distillation, the three-component mixture may have a concentration in the vicinity of the distillation boundary line B-C. In the case of such a composition, it may even be sufficient for only a small TBA-containing stream together with a part of the product obtained as distillate at the top of the column to be added to the industrial mixture, since the composition of the mixture can also be shifted into the distillation field 2 in this way.

The fractional distillation of streams obtained in the process of the invention, in particular the mixture to which a TBA-containing stream has been added, can be carried out in one or more column(s) provided with internals which may be trays, rotating internals, random packing and/or ordered packing. The separation by distillation of this mixture is preferably carried out in a single column.

In the case of column trays, the following types can be used:

trays having holes or slits in the plate;

trays having necks or chimneys which are covered by bills, caps or hoods;

trays having holes covered by movable valves in the plate;

trays having a special construction.

In columns having rotating internals, the internal reflux is either sprayed by means of rotating funnels or is spread as a film over a heated tube wall by means of a rotor.

Different beds of various packing elements can be used in the columns employed in the process of the invention. They can be made of virtually any materials, e.g. steel, stainless steel, copper, carbon, stoneware, porcelain, glass, plastics, etc., and have various shapes, e.g. spheres, rings having smooth or profiled surfaces, rings having internal webs or holes in the wall, wire mesh rings, saddles and spirals.

Packing having a regular geometry can comprise, for example, sheets or woven meshes of metal or plastic. Examples of such packing are Sulzer Gewebepackungen BX, Sulzer Lamellenpackungen Mellapak made of sheet metal, high-performance packing such as MellapakPlus, structured packing from Sulzer (Optiflow), Montz (BSH) and Kuihni (Rombopak).

The column (2) for the preliminary dewatering of the industrial mixture used as starting material preferably has from 3 to 50 theoretical plates, in particular from 6 to 40 theoretical plates. The feed plate depends on the composition of the mixture in the distillation field 1. The feed is preferably introduced onto the 2nd to 55th, counted from the top, theoretical plate, in particular onto the 3rd to 35th theoretical plate.

The column used for separation of the mixture obtained by addition of the TBA-containing stream preferably has from 5 to 70 theoretical plates, preferably from 10 to 60 theoretical plates. The feed plate depends on the composition of the mixture. It has been found to be advantageous for the mixture to be fed onto the 2nd to 55th, counted from the top, theoretical plate, in particular onto the 3rd to 35th theoretical plate.

The operating pressure of the columns (2) and (6) is preferably from 0.01 to 15 bar abs. (bara). The two columns for separating off water from the industrial mixture prior to the addition of the TBA-containing stream (preliminary column) and the column for fractionally distilling the mixture obtained after addition of the TBA-containing stream are operated at the same pressure or different pressures. In the case of the pressure being the same, the columns are preferably operated at from 0.5 to 10 bara, while in the case of different pressures the pressure in the preliminary column is preferably in the range from 0.5 to 10 bara and that in column (6) is preferably in the range from 0.1 to 10 bara.

Distillation of the mixture obtained by addition of the TBA-containing stream gives a bottom product comprising 2-butanol and possibly high boilers. The TBA content of this stream is preferably less than 2% by mass, more preferably less than 1.7% by mass. A mixture of TBA, water and any low boilers is taken off at the top. The 2-butanol content of the top product is preferably less than 4% by mass, in particular less than 3% by mass. 2-Butanol which is free or virtually free of high boilers can be obtained by taking off the 2-butanol from the vapor phase of the vaporizer or in gaseous or liquid form as side stream in the stripping section of the column.

The TBA fractions separated from the mixture by means of the process of the invention can be employed for known purposes. For example, they can serve as starting material for the preparation of isobutene. Any low boilers present therein can be separated off by distillation.

The 2-butanol which has been separated off can be utilized for customary industrial applications. Thus, for example, it can be used as precursor for methyl ethyl ketone, as solvent for surface coatings and resins, as a constituent of brake fluids and as a constituent of cleaners. Furthermore, it is employed in the production of fragrances, dyes and wetting agents.

The process of the invention enables 2-butanol to be separated off from any ternary mixtures of TBA, SBA and water lying in the distillation field 1 without losses of TBA. This succeeds even when the mixtures further comprise up to 5% by mass of high boilers (e.g. C8- or C12-hydrocarbons formed by oligomerization of isobutene, C8-alcohols) and/or low boilers (e.g. isobutene or other C4-hydrocarbons). Thus, 2-butanol, in particular 2-butanol having a tert-butanol content of less than 1% by mass, preferably less than 0.5% by mass, can be prepared by means of the process of the invention.

In particular, TBA streams enriched in 2-butanol from plants in which isobutene is prepared from TBA by elimination of water are used in the process of the invention. These streams usually further comprise C4-hydrocarbons and downstream products of C4-olefins as additional components.

Figure 2:
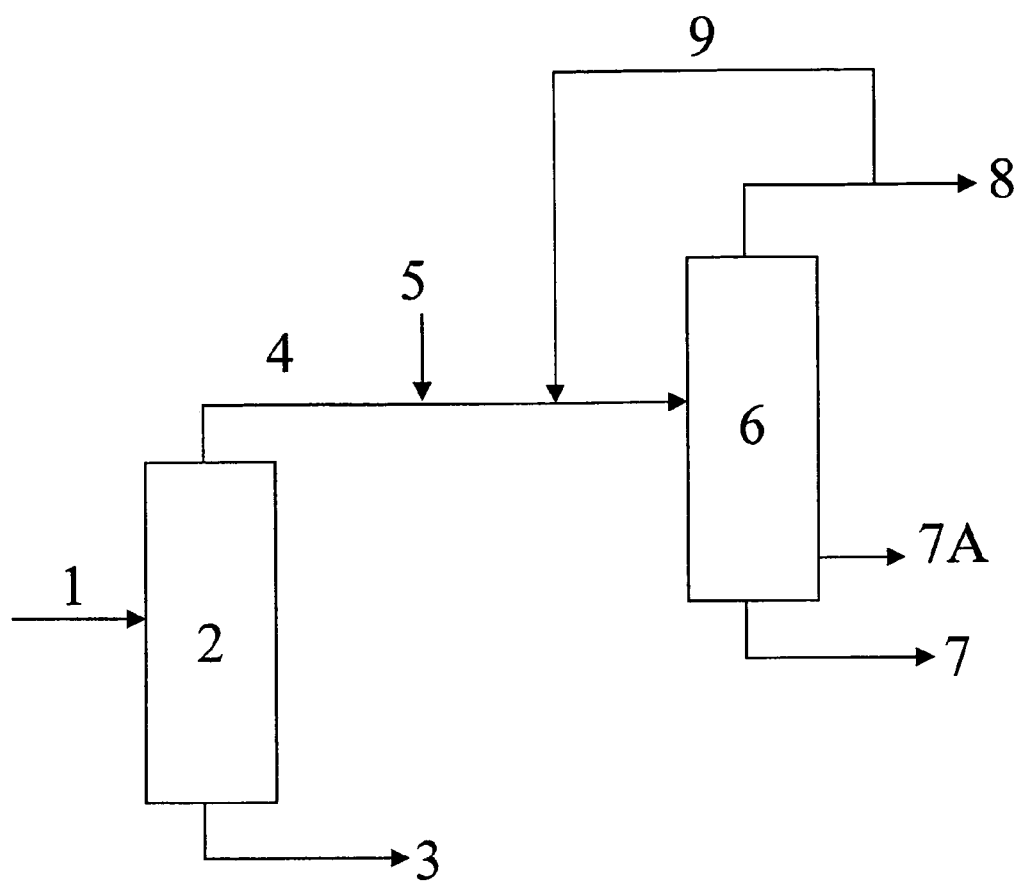
FIG. 2 depicts a block diagram of a plant in which a specific embodiment of the process of the invention can be carried out.

A block diagram of a plant in which a specific embodiment of the process of the invention can be carried out is shown in FIG. 2. The industrial mixture (1) serving as starting material, which has a composition in the distillation field 1, is firstly worked up in a column (2), also referred to as preliminary column, in such a way that a water-rich stream (3) is discharged at the bottom of the preliminary column. A TBA-containing stream (5) is then added to the industrial mixture (4) which has been partly dewatered in this way but still has a composition in the distillation field 1 in such an amount that the mixture obtained has a composition which lies in the distillation field 2. If desired, a part (9) of the distillate (8) from column (6) can be added to this mixture, but in such an amount that the addition of the stream does not alter the composition to such an extent that it no longer lies in the distillation field 2. This mixture is fed into the column (6) and in this is separated into a bottom product (7) comprising the 2-butanol to be separated off and a top product (8) comprising TBA, water and possibly low boilers. All or part of the distillate stream (8) can be reused directly as feed to a TBA dissociation. Column (6) is optionally operated at a pressure different from that in column (2). To obtain 2-butanol having a low content of high boilers, this product can be taken off from the vapor phase of the vaporizer or in gaseous or liquid form as a side stream (7A) from the stripping section of the column (6).

To operate the process of the invention in its simplest variant, the column (2) is omitted and a TBA-containing stream (5) is added directly to the industrial mixture in such an amount that the composition of the mixture lies in the distillation field 2. This stream is once again optionally admixed with stream (9) before being fed into the column (6) and worked up as described above.

Ordinary components such as pumps, compressors, valves, heat exchangers and vaporizers are not shown in the block diagrams, but are of course components of a plant.

The following example illustrates the invention without restricting its scope which is defined by the description and the claims.

EXAMPLE

SBA was separated off in a plant of the type shown in FIG. 2 with the streams (7A) and (9) being ommitted. The diameter of the column (2) is 50 mm. Metal distillation packing having 12 theoretical plates was installed, and the feed was introduced onto the 7th theoretical plate counted from the top. The diameter of the column (6) was likewise 50 mm. Metal distillation packing having 20 theoretical plates was installed, and the feed was introduced onto the 6th theoretical plate counted from the top. The feed (1) was taken from the industrial plant and used for the experiments. The stream numbers in the following table are the same as those in FIG. 2. The distillate (4) from the column (2) was collected and part of it was used as feed to the second column (6). Components having a concentration below 0.1 parts by mass in the mixture generally not shown in the table.

| Stream number | Stream name | Mass flow [kg/h] | Concentration of the stream, in parts by mass |
|---|---|---|---|
| 1 | Fresh feed | 1.80 | Water 63.5<br>TBA 30.2<br>2-Butanol 4.5<br>$C_8$-Alcohol 1.7<br>Other components 0.1 |
| 3 | Wastewater | 1.03 | Water 96.9<br>TBA 0.1<br>2-Butanol 0.1<br>$C_8$-Alcohol 2.9 |
| 4 | Dewatered mixture, distillate from column (2) | 0.77 | Water 18.9<br>TBA 70.3<br>2-Butanol 10.4<br>$C_8$-Alcohol 0.1<br>Other components 0.3 |
| 4 | Dewatered mixture, feed to column (6) | 0.75 | Water 18.9<br>TBA 70.3<br>2-Butanol 10.4<br>$C_8$-Alcohol 0.1<br>Other components 0.3 |
| 5 | Fresh TBA | 0.75 | Water 0.004<br>TBA 99.8<br>2-Butanol 0.15<br>$C_8$-Alcohol 0.01<br>Other components 0.036 |
| 7 | Bottoms from column (6) | 0.08 | TBA 0.3<br>2-Butanol 96.7<br>C8-Alcohol 1.2<br>Other components 1.9 |
| 7A | Side stream taken off from column (6) | omitted | |
| 8 | Distillate from column (6) | 1.42 | Water 10.0<br>TBA 89.6<br>2-Butanol 0.4<br>Other components 0.1 |
| 9 | Recycle stream | omitted | |

Column (2) was operated at 1 bar abs. and a reflux ratio of 3.5. Column (6) was operated at 1 bar abs. and a reflux ratio of 4.

As can be seen from table 1, the process of the invention makes it possible for SBA to be separated off in a simple manner, with the losses of TBA being limited to the small proportion in the product from the top of the column.

Obviously, numerous modifications and variations of the present invention are possible in light of the above teachings. It is therefore to be understood that within the scope of the appended claims, the invention may be practiced otherwise than as specifically described herein.

This application claims priority to DE 10312918, which was filed Mar. 22, 2003, the entire contents of which are incorporated herein by reference.

The invention claimed is:

1. A process for separating 2-butanol from an industrial mixture which comprises 2-butanol, tert-butanol and water, wherein the proportion by mass of water is greater than the limit concentration of the distillation boundary line connecting an azeotrope of tert-butanol and water; and an azeotrope of 2-butanol and water, comprising
    adding tert-butanol to the industrial mixture to reduce the concentration of water such that the proportion by mass of water is less than the limit concentration of the distillation boundary line connecting an azeotrope of tert-butanol and water; and an azeotrope of 2-butanol and water; and
    separating the mixture by distillation into a stream comprising 2-butanol and a stream comprising tert-butanol and water.

2. The process as claimed in claim 1, wherein the tert-butanol is added in a stream, which has a water content of less than 12% by mass.

3. The process as claimed in claim 2, wherein the tert-butanol is added in a stream, which has a water content of less than 5% by mass.

4. The process as claimed in claim 1, which further comprises removing water from the industrial mixture in a column before adding the tert-butanol.

5. The process as claimed in claim 1, which further comprises adding a part of the stream comprising tert-butanol and water to the industrial mixture.

6. The process as claimed in claim 1, wherein the industrial mixture has a water content of less than 10% by mass, based on the concentration of tert-butanol, 2-butanol and water in the industrial mixture.

7. The process as claimed in claim 1, wherein the stream comprising 2-butanol obtained after separating the mixture comprises less than 1% by mass of tert-butanol.

8. The process as claimed in claim 1, wherein the stream comprising 2-butanol obtained after separating the mixture comprises less than 0.5% by mass of tert-butanol.

9. The process as claimed in claim 1, wherein the separating of the stream comprising 2-butanol comprises taking a vapor phase of a vaporizer of a column; or a gaseous or liquid as a side stream in a stripping section of the column.

10. The process as claimed in claim 9, which further comprises removing water from the industrial mixture in a column before adding the tert-butanol; wherein the column for removing water from the industrial mixture is operated at a different pressure than the column for separating the stream comprising 2-butanol.

11. The process as claimed in claim 1, wherein the proportion of water in the industrial mixture is less than 11% by mass when the concentration of 2-butanol is from 0.0001 to 6% by mass.

12. The process as claimed in claim 11, wherein the proportion of water in the industrial mixture is less than 10% by mass.

13. The process as claimed in claim 11, wherein the proportion of water in the industrial mixture is less than 9.5% by mass.

14. The process as claimed in claim 1, wherein the proportion of water in the industrial mixture is less than 14% by mass when the concentration of 2-butanol is from 6.01 to 15% by mass.

15. The process as claimed in claim 14, wherein the proportion of water in the industrial mixture is less than 13% by mass.

16. The process as claimed in claim 1, wherein the tert-butanol is added in a stream and wherein the stream comprises from 90 to 99.99% tert-butanol.

* * * * *